United States Patent [19]

Zdarsky

[11] Patent Number: 4,643,674
[45] Date of Patent: Feb. 17, 1987

[54] HOLDING ARRANGEMENT FOR DENTAL HAND INSTRUMENTS

[75] Inventor: Eduard Zdarsky, Munich, Fed. Rep. of Germany

[73] Assignee: Vereinigte Dentalwerke Antaeos-Beutelrock Zipperer Zdarsky Ehr-GmbH & Co. KG, Munich, Fed. Rep. of Germany

[21] Appl. No.: 769,008

[22] Filed: Aug. 23, 1985

[30] Foreign Application Priority Data

Aug. 28, 1984 [DE] Fed. Rep. of Germany ....... 3431598

[51] Int. Cl.⁴ .............................................. A61C 5/02
[52] U.S. Cl. ................................... 433/102; 63/1 R
[58] Field of Search ................. 433/102, 141; 63/1 R

[56] References Cited

U.S. PATENT DOCUMENTS

| 1,087,015 | 2/1914 | Heylmun | 63/1 R |
| 1,517,934 | 12/1924 | Anderson | 63/1 R |
| 1,521,051 | 12/1924 | Shiba | 63/1 R |
| 2,138,640 | 11/1938 | Levy | 63/1 R |
| 3,330,040 | 7/1967 | Kahn | 433/102 |
| 3,901,251 | 8/1975 | Johnston | 132/91 |
| 4,280,808 | 7/1981 | Johnsen et al. | 433/141 |
| 4,321,040 | 3/1982 | Miller et al. | 433/102 |

FOREIGN PATENT DOCUMENTS

| 2502928 | 7/1976 | Fed. Rep. of Germany | 433/141 |
| 759648 | 2/1934 | France | 433/102 |

*Primary Examiner*—John J. Wilson
*Attorney, Agent, or Firm*—Max Fogiel

[57] ABSTRACT

In a manually operated instrument such as a root-canaling instrument, a security cord (10) is attached at one end to the handle (1) of the instrument by means of a mounting shell (5), which can be snapped onto and seated against the handle from the shaft end of the instrument, and at the other end to a ring (13) on the operating dentist's finger.

The security cord (10) is attached to the finger ring (13) with a wrapping or clamping device (15) and can be released.

14 Claims, 6 Drawing Figures

U.S. Patent  Feb. 17, 1987  4,643,674
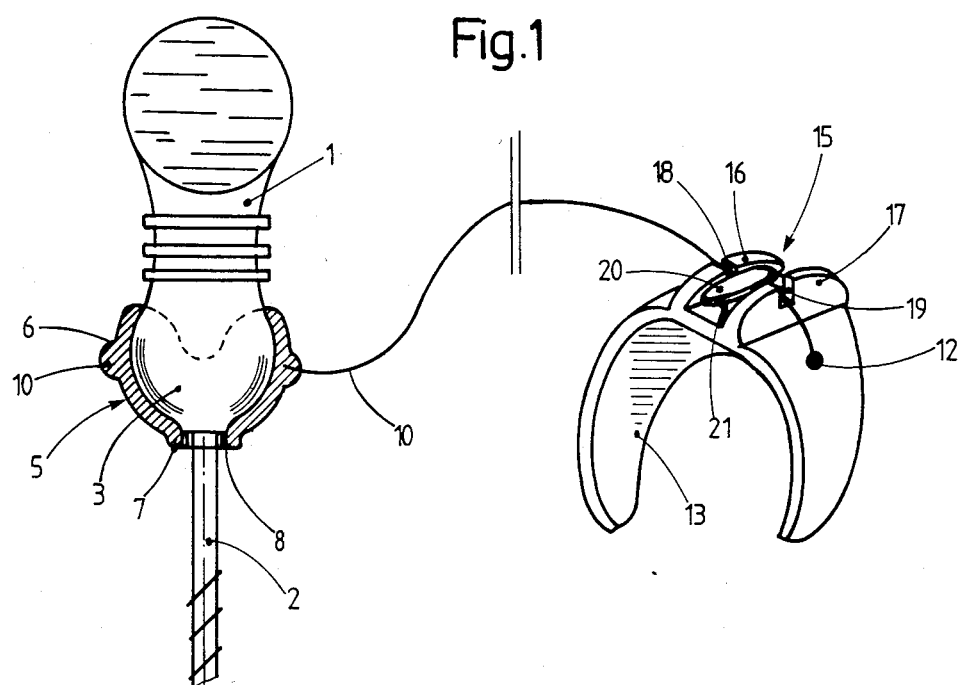
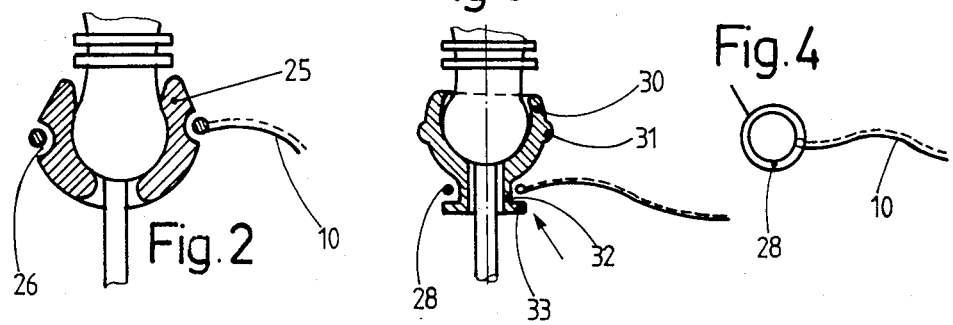
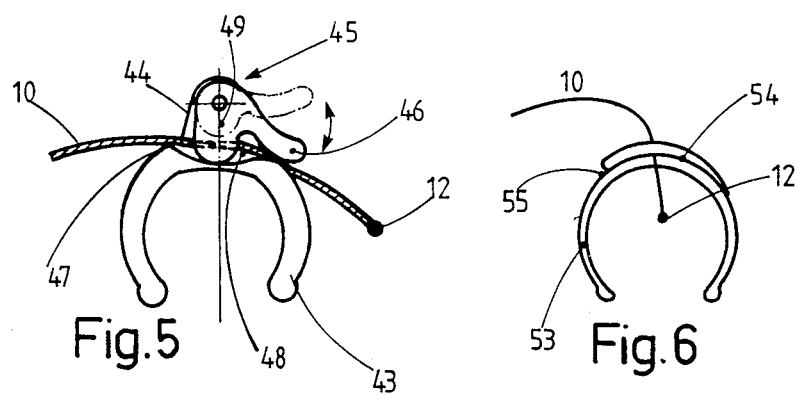

HOLDING ARRANGEMENT FOR DENTAL HAND INSTRUMENTS

DESCRIPTION

The invention concerns a retainer for manually operated medical and particularly dental instruments such as root-canaling instruments.

Manually operated instruments are usually employed in root-canal treatments. Unavoidable impediments to the motion of the dentist's hands within the oral cavity and increased salivation lead to a risk of the instrument dropping from the dentist's fingers and falling into the oral cavity. The results are especially bad when the patient is recumbent. Retainers that secure the instrument with a chain or cord have already been created in practice to avoid such accidents. The security cord is attached to the instrument with a screw-on sleeve. Since, however, tools of five to ten different sizes and possibly of several different types as well must often be utilized in prepering the canal, screwing the sleeves on and off takes a lot of time, which the patient must endure with open mouth. It is also troublesome to screw the usually very small parts together. Another retainer with a transverse bore in the handle of the instrument and terminating in an open notch is also known (German OS NO. 2 502 928). One end of the security cord is connected to a finger ring and the other end supports a catch bar that can in the wrapped position be inserted through the bore in the handle and positioned in the notch. Although this device does avoid the screw-on sleeve and hence increasing the size of the handle, the notch in the handle is an undesirable depression that dirt can accumulate in. Threading the security cord demands a high level of patience and skill. Furthermore, it has turned out that the catch bar can easily come out of the notch and make the dentist's work more difficult. The problems associated with the known retainers accordingly result in the security measures usually having to be done completely without.

The object of the present invention is to provide a retainer for manually operated medical and particularly dental instruments such as root-canaling instruments that will ensure simple and rapid securing of the instruments along with dependable operation on the part of the dentist.

The mounting shell in accordance with the invention represents a simple, inexpensive, and reliable retainer for the security cord. The cord can either be directly molded into the shell or fastened to it subsequently in specially provided continuous grooves or similar structures. Since the relatively thin-walled mounting shell is snapped over the handle at the shaft end of the instrument, it will in no way affect the handling of the instrument. Since the shell is also especially appropriate for snapping over the handle mechanically and hence for being mounted while the instrument is being manufactured, it can be supplied along with the instrument, simplifying and abbreviating preparation time on the part of the dentist. Since a mounting shell that is mounted during the manufacturing process can be color coded, it is also possible to code the different instruments in accordance with size, type, sequence of utilization, etc.

It is especially practical to add an X-ray contrast agent to the material that the mounting shell is made out of to provide a reliable reference point during any X-ray progress photographs taken before or during the treatment.

The security cord is attached to the dentist's finger with a securing anchor that is built onto a finger ring and that secures the end of the cord either by clamping or with a catch loop. The cored can therefore be rapidly secured to and released from the dentist's finger without special expenditure. This mode of attachment also makes it possible to equalized the length of the cord between the ring and the instrument and hence adjust to different situations.

Further characteristics of the invention are recited in the subsidiary claims.

The invention will now be described with reference to embodiments that are illustrated schematically in the drawing, wherein FIG. 1 is a partial section through a root-canal instrument with a retainer in accordance with the invention, FIG. 2 is a section through another mounting shell, FIG. 3 is a section through still another mounting shell, FIG. 4 illustrates a security cord with a fastening ring, FIG. 5 is a side view of a finger ring with a cam-driven clamp, and FIG. 6 illustrates a finger ring with a compression spring.

A mounting shell 5 has been snapped over an accommodation ball 3 at the bottom of the handle 1 of a dental root-canal instrument from the direction of the shaft 2 of the instrument. Shell 5 is thin-walled and is made out of an elastic and inert plastic, tightly seated against handle 1. The mounting shell 5 illustrated in FIG. 1 has around it a continuous bead 6 that makes it easier to get a grip on while it is being snapped on and off. An aperture collar 7 defines a mounting aperture 8. A security cord 10 is in this embodiment molded into continuous bead 6 and accordingly fastened to mounting shell 5 in such a way that it cannot be released from it. The other end 12 of the cord, which is thickened for example into a terminal head, leads to a finger ring 13, which the dentist places on an appropriate finger. Ring 13 is equipped with a securing anchor 15 that consists of two cheeks 16 and 17 of anchor 15 and of insertion slots 18 and 19. Between the cheeks is an anvil 20. The cord is threaded through insertion slots 18 and 19 and wrapped around the neck 21 of anvil 20. The free end of the cord can accordingly be attached to the ring very easily and rapidly while being adjusted to any desired length. Terminal head 12 is in a practical way too thick to pass through the slots.

The non-release attachment of security cord 10 to mounting shell 5 is especially practical when the shell has been snapped onto the handle while the instrument was being initially manufactured by the producer or supplier. In this case mounting shell 5 and security cord 10 will remain attached to the instrument and will be sterilized or thrown away along with it subsequent to use. The shell can however also be snapped off during the course of the dental practice and replaced with another.

FIGS. 2 and 3 illustrate other types of mounting shell. The mounting shell 25 illustrated in FIG. 2 is more or less in the form of a hollow ball and has around it a continuous groove 26 that security cord 10 can be inserted and fastened in and removed from. The security cord 10 illustrated in FIG. 4 is in a practical way attached to a fastening ring 28, with the end of the cord molded into or tied onto it. This type of fastening ring 28 is snapped onto a mounting shell 30 that has an accommodation bead 31 around it. At the aperture end are a cord depression 32 and a depth-adjustment flange 33 that constitutes a precisely adjustable abutment for measuring the depth into the root canal.

The mounting shell conforms to the shape of the handle. If the handle lacks a spherical or other expansion at the shaft end, seating can be ensured by making the wall of the shell more elastic.

FIG. 5 illustrates another type of finger ring 43 and securing anchor 45. An anchor cam 47 that pivots on one cheek 44 can be lifted by means of a finger grip 46 that extends in the closed position into a finger depression 48 and forms an exterior demarcation. An inner cam 49 forces in this position the security cord down against the finger ring and prevents it from being pulled through. This anchor also makes it possible to rapidly and reliably secure the cord at any desired length. It is especially easy to insert and release just by pivoting the cam up.

An especially simple means of retaining security cord 10 results in conjunction with a finger ring 53 that has a compression spring 54. The cord can be threaded between spring 54 and ring 53 from open end 55 and retained in position by the force of the spring. The cord can be prevented from being withdrawn unintentionally from clamping gap 55 during the course of an operation both by increasing the spring force and by wearing the ring in a position in which the gap does not open in the direction of tension.

Since all parts are made out of a material that can be sterilized, they can be sterilized either by themselves or along with other accessories.

It is practical to add an X-ray contrast agent to the material that the mounting shell is made out in order to make the silhouette of the instrument visible and provide reference points for measurement and other indications.

The finger rings illustrated herein can also of course be manufactured continuous. Since the ring is an independent component and can accordingly be made very stable, it thoroughly lends itself to precise adjustment to the dentist's particular finger.

I claim:

1. A retainer for manually operated medical and particularly dental instruments such as root-canaling instruments, comprising: an instrument having a handle with an end and a working shaft end; a ring for mounted on a finger of an operating dentist; a security cord attached at one end to said handle end and at the other end to said ring; a mounting shell for attaching said security cord to said handle end, said mounting shell having means for snapping the mounting shell onto and seated against said handle, and having means for allowing the mounting shell to pass over said shaft end, whereby said mounting shell can be attached to said handle from the shaft end of the instrument.

2. A retainer as defined in claim 1, including wrapping means for attaching releasably said ring on the finger of the operating dentist to said security cord.

3. A retainer as defined in claim 1, including clamping means for attaching releasably said ring on the finger of the operating dentist to said security cord.

4. A retainer as defined in claim 1, wherein said mounting shell has a continuous bead around it.

5. A retainer as defined in claim 1, wherein said mounting shell is comprised of a material having an X-ray contrast agent added thereto.

6. A retainer as defined in claim 1, wherein said security cord is molded into said mounting shell.

7. A retainer as defined in claim 1, wherein said mounting shell has a continuous groove around it.

8. A retainer as defined in claim 7, including an elastic ring which can be introduced into said continuous groove on said mounting shell, the end of said security cord to be attached to said mounting shell being attached to said elastic ring.

9. A retainer as defined in claim 1, wherein said mounting shell has a depression for holding said cord and a measuring flange.

10. A retainer as defined in claim 9, including an elastic ring which can be introduced into said depression on said mounting shell, the end of said security cord to be attached to said mounting shell being attached to said elastic ring.

11. A retainer as defined in claim 1, wherein said mounting shell is color coded.

12. A retainer as defined in claim 1, wherein said ring for mounting on the finger of the operating dentist has a securing anchor with a wrapping anvil for attaching said security cord.

13. A retainer as defined in claim 1, wherein said ring for mounting on the finger of the operating dentist has a clamping cam.

14. A retainer as defined in claim 1, wherein said ring for mounting on the finger of the operating dentist has a spring clamp.

* * * * *